(12) United States Patent
Nun et al.

(10) Patent No.: US 8,563,010 B2
(45) Date of Patent: Oct. 22, 2013

(54) METHOD FOR PREVENTING MOLD FORMATION BY USING HYDROPHOBIC MATERIALS, AND MOLD-CONTROLLING AGENT FOR BUILDING PARTS

(75) Inventors: Edwin Nun, Billerbeck (DE); Andreas Eisenreich, Koenigsbrunn (DE)

(73) Assignee: Evonik Degussa GmbH, Essen (DE)

( * ) Notice: Subject to any disclaimer, the term of this patent is extended or adjusted under 35 U.S.C. 154(b) by 1555 days.

(21) Appl. No.: 10/551,841

(22) PCT Filed: Feb. 9, 2004

(86) PCT No.: PCT/EP2004/050099
§ 371 (c)(1),
(2), (4) Date: Feb. 2, 2007

(87) PCT Pub. No.: WO2004/086867
PCT Pub. Date: Oct. 14, 2004

(65) Prior Publication Data
US 2007/0184981 A1    Aug. 9, 2007

(30) Foreign Application Priority Data
Apr. 3, 2003 (DE) .................................. 103 15 128

(51) Int. Cl.
*B05D 3/00* (2006.01)
*B05D 5/02* (2006.01)

(52) U.S. Cl.
USPC ........ 424/400; 427/256; 427/372.2; 427/384; 427/397.7

(58) Field of Classification Search
None
See application file for complete search history.

(56) References Cited

U.S. PATENT DOCUMENTS

| | | | |
|---|---|---|---|
| 6,811,856 B2 | 11/2004 | Nun et al. | |
| 6,852,389 B2 | 2/2005 | Nun et al. | |
| 6,858,284 B2 | 2/2005 | Nun et al. | |
| 6,955,834 B2 * | 10/2005 | Rohrbaugh et al. | 427/180 |
| 6,977,094 B2 | 12/2005 | Oles et al. | |
| 7,066,998 B2 * | 6/2006 | Rohrbaugh et al. | 106/286.5 |
| 2002/0016433 A1 * | 2/2002 | Keller et al. | 528/10 |
| 2002/0148601 A1 | 10/2002 | Roos et al. | |
| 2002/0150723 A1 | 10/2002 | Oles et al. | |
| 2002/0164443 A1 | 11/2002 | Oles et al. | |
| 2003/0013795 A1 | 1/2003 | Nun et al. | |
| 2003/0108716 A1 | 6/2003 | Nun et al. | |
| 2003/0134086 A1 | 7/2003 | Nun et al. | |
| 2003/0147932 A1 | 8/2003 | Nun et al. | |
| 2004/0081818 A1 * | 4/2004 | Baumann et al. | 428/323 |
| 2004/0154106 A1 | 8/2004 | Oles et al. | |
| 2005/0084653 A1 | 4/2005 | Nun et al. | |
| 2005/0103457 A1 | 5/2005 | Nun et al. | |
| 2005/0112326 A1 | 5/2005 | Nun et al. | |
| 2005/0118433 A1 | 6/2005 | Oles et al. | |
| 2005/0163951 A1 | 7/2005 | Oles et al. | |
| 2005/0167877 A1 | 8/2005 | Nun et al. | |
| 2005/0205830 A1 | 9/2005 | Oles et al. | |
| 2005/0208269 A1 | 9/2005 | Nun et al. | |
| 2005/0227045 A1 | 10/2005 | Oles et al. | |
| 2005/0253302 A1 | 11/2005 | Nun et al. | |
| 2006/0049376 A1 | 3/2006 | Nun et al. | |

FOREIGN PATENT DOCUMENTS

| | | |
|---|---|---|
| DE | 37 30 820 | 8/1988 |
| DE | 199 13 738 | 11/2000 |
| DE | 199 55 153 | 5/2001 |
| DE | 101 39 574 | 2/2003 |
| EP | 0 933 388 | 8/1999 |
| EP | 0 990 015 | 4/2000 |
| EP | 1 283 077 | 2/2003 |
| JP | 08165208 A * | 6/1996 |
| WO | 96/04123 | 2/1996 |
| WO | WO 0119932 A2 * | 3/2001 |
| WO | 01/48098 | 7/2001 |
| WO | 02/084013 | 10/2002 |
| WO | 03/013748 | 2/2003 |
| WO | 03/066241 | 8/2003 |
| WO | 2004/007625 | 1/2004 |
| WO | 2004/039909 | 5/2004 |

OTHER PUBLICATIONS

Patankar, Mimicking the lotus effect: Influence of double roughness structures and slender pillars, Langmuir (2004), vol. 20, No. 19, pp. 8209-8213.*
Nun et al., Lotus-Effect-Surfaces, Macromol. Symp. (2002), vol. 187, pp. 677-682.*
U.S. Appl. No. 10/526,559, filed Mar. 4, 2005, Nun, et al.
U.S. Appl. No. 10/546,979, filed Aug. 26, 2005, Nun, et al.
U.S. Appl. No. 11/321,285, filed Dec. 21, 2005, Oles, et al.
U.S. Appl. No. 11/312,557, filed Dec. 21, 2005, Oles, et al.
U.S. Appl. No. 10/556,092, filed Nov. 9, 2005, Oles, et al.
U.S. Appl. No. 11/312,469, filed Dec. 21, 2005, Nun, et al.
Barthlott et al. "Purity of the sacred lotus, or escape from contamination in biological surfaces", Planta, vol. 202, pp. 1-8, XP000925073 1997.
Kosmetische Verordnung, vol. 7, BGBl. 1 S. 2410 1997.
DIN 53 206 1972.

* cited by examiner

*Primary Examiner* — James H Alstrum Acevedo
*Assistant Examiner* — Frank Choi
(74) *Attorney, Agent, or Firm* — Oblon, Spivak, McClelland, Maier & Neustadt, L.L.P.

(57) ABSTRACT

The present invention relates to a method for suppressing mold formation on building parts using hydrophobic substances, wherein a dispersion of hydrophobic particles having a mean particle diameter of from 0.005 to 5 μm in an organic dispersant is applied to the surface to be protected from mold attack and the dispersant is then removed, and to a composition for building parts which inhibits mold growth and comprises from 0.1 to 10% by weight of hydrophobic particles having a mean particle diameter of from 0.005 to 5 μm dispersed in an organic dispersant.

17 Claims, 2 Drawing Sheets

METHOD FOR PREVENTING MOLD FORMATION BY USING HYDROPHOBIC MATERIALS, AND MOLD-CONTROLLING AGENT FOR BUILDING PARTS

CROSS-REFERENCE TO RELATED APPLICATIONS

This application is the national-stage under §371 of PCT/EP04/50099, filed Feb. 9, 2004. It also claims priority under §119 to Germany 103 15 128.1, filed Apr. 3, 2003.

BACKGROUND OF THE INVENTION

1. Field of the Invention

The present invention relates to a method for suppressing mold formation on building parts using hydrophobic substances, and to a composition for building parts which inhibits mold growth.

An increased tendency to condensation or excessively high atmospheric humidity in rooms may have various causes. In the kitchen and bathroom, there are extreme and brief peak loads with respect to atmospheric humidity, during which condensation of the water vapor can scarcely be avoided. Such atmospheric humidity can arise, for example, through cooking, dishwashing, bathing, showering, washing or drying laundry. Long-lasting water vapor loads can also occur in bedrooms. Up to one liter of water evaporates from a person per night. This amount of water is sufficient to increase the atmospheric humidity of an approximately 50 m² room of customary room height at a temperature of 20° C. from a given atmospheric humidity of 60% to 100%. Particularly in the area of cold bridges and/or poor external insulation, condensation may form. This condensation in turn promotes the growth of fungi. Molds require a temperature of about 20° C. and an atmospheric humidity of more than 70% for growth.

As a result of the installation of new, well insulated windows in old buildings, the condensation no longer collects on the cold single glazing, from which it subsequently runs off, but rather the condensation is deposited on the inside of the comparatively colder outer walls of the room. Mold formation, for example on roller shutter boxes or in corners of rooms, is the result. Attack by molds in new buildings also occurs as a result of constructional deficiencies, for example if the building has cold bridges in the masonry owing to constructional deficiencies.

Mold comprises fungi which populate the wall and other materials, first superficially and subsequently also deeply. Mold spots are individual, generally round fungal colonies which have germinated from a single spore. Fungus researchers distinguish about 10 000 mold varieties, only a few of which, however, are found in living rooms. There is no wall mold. Different varieties, especially the Aspergillus and Penicillium varieties, coexist in a complex manner.

In contrast to plants, fungi have no chlorophyll and are therefore not capable of obtaining their energy from sunlight. Wood or wood components, wall paints, gypsum-based plaster, flowerpot earth and dead parts of indoor plants and food serve as an energy source for fungi in the living area. Like all living beings, fungi too require water in order to thrive. If there is a lack of water, the fungus dies but does not do so immediately and instead forms so-called permanent cells. These enable the fungus to survive emergency periods. If favorable growth conditions are present again, such as, for example, sufficient humidity, it continues to growth if the "emergency period" was not sufficiently long. The spread and multiplication of the fungi take place via spores and conidia. They are produced in an unimaginable large number and spread by floating in the air. Their diameter is between 0.002 and 0.006 mm and they are therefore invisible to the human eye. However, germination and fungal growth occur only under growth conditions favorable for the respective fungus variety. Damp walls, for example, therefore constitute an ideal living space and culture medium for fungi.

It is therefore of very great economic interest to reduce the consequences of mold attack. The first visible consequences of mold attack are the occurrence of discolorations, so-called mold spots. These are initially small and point-like and then become larger and finally grow into a fungal lawn. After a relatively long-lasting attack, the affected building materials are destroyed. Wallpapers disintegrate, wood and paper become brittle, and plaster and paint peel off.

In order to prevent a building from being attacked by molds, constructional measures are required in order to avoid cold bridges and hence condensation of atmospheric humidity, for example on the inner surfaces of outer walls. These constructional measures are supported by ventilation or air purification measures. Thus, a high air exchange rate is advisable, i.e. the total room air should be exchanged at least once per hour.

2. Description of Related Art

One of the possible constructional measures for avoiding mold attack comprises moisture-storing plaster coats which are applied to the inner surface of a room. These plaster coats release the moisture to the environment again as soon as the atmospheric humidity of the environment has decreased. This makes it possible to prevent the walls from being permanently wet and hence mold attack occurring. Such moisture-storing plaster materials are available from epasit GmbH Spezialbaustoffe under the trade name Epatherm®.

The patent DE 199 13 738 C2 describes a method for stopping mold growth on the inner surfaces of a room. Here, the surface temperature of the inner surface of a room is increased to a temperature above the dew point by heat energy supplied directly to this surface. The resulting temperature difference between the surface temperature of the inner surface of a building wall and the room air temperature is dependent on the temperature and the atmospheric humidity of the environment. A disadvantage here is the high energy consumption.

Patent application DE 101 39 574 describes self-cleaning surfaces which have antimicrobial properties. The antimicrobial property is achieved by virtue of the fact that the coating material also comprises antimicrobial polymers in addition to the structure-forming particles. These surfaces inhibit the growth of bacteria, fungi and algae. However, this method has the disadvantage that expensive antimicrobially active polymers have to be used.

The Laid-Open Applications DE 199 55 153 A1 and DE 199 57 102 A1 describe the addition of 4-hydroxybenzoic esters and/or sodium alkyl-4-hydroxybenzoates as mold-inhibiting active substances in synthetic resin emulsions or in joint mortar. 4-Hydroxybenzoic esters—so-called parabens—are considered in principle to be safe. Thus, they are approved as preservatives up to a content of 0.4% by weight (cosmetics regulation of Oct. 7, 1997, German Federal Law Gazette 1 page 2410). Owing to the low molecular weight character of the parabens, they may be leached by means of the condensation forming at a cold bridge.

A wall lining material for buildings having a mold-preventing effect is described by the laid-open application DE 37 30 820. N-(Fluorodichloromethylthio)-phthalimide and N,N-dimethyl-N'-phenyl-N'-(fluoro-dichloromethylthio) sulfamide are mentioned as a preferred composition for preventing fungal attack. These ingredients were assigned only slight toxicological potential in a study by the International Programme on Chemical Safety, IPCS, carried out in 1974, but the disadvantageous ecological aspects of the introduction of halogenated compounds into the environment had not been taken into account there. Whether building materials which contain the mold-preventing substances described in DE 37 30 820 are capable of being recycled or whether they have to be deposited in landfills is furthermore unclear.

In their PCT Application WO 01/48098, the Deutsche Amphibolin-Werke von Robert Murjahn GmbH & Co. KG describe an aqueous coating material having a dirt- and water-repellent effect, which contains synthetic sheet silicates and/or colloidal silica having primary particle sizes of in each case less than 500 nm. The colloidal particles have been rendered hydrophobic and/or oleophobic on their surfaces. The coating material may contain fungicides as a functional substance. This method can scarcely be used subsequently since a large amount of energy is required both in the preparation of the hydrogel and in the drying thereof at a relatively high temperature over several days.

The abovementioned methods for suppressing mold formation in buildings according to the prior art have the disadvantage that the cold bridges in a building have to be recognized in good time. Frequently, the potential cold bridges of a building are not recognized at an early stage in the planning, construction, restoration or renovation phase. The subsequent elimination of these cold bridges of a completed building is as a rule feasible only at considerable expense or may not be feasible at all. Until the causes of the cold bridges are eliminated by constructional measures, there is, according to the prior art, only the possibility of using fungicides or wall lining materials, such as wallpaper and wall paints, which comprise fungicides. The effect of these fungicides on humans is often not yet clear, or said fungicides have an effect on humans which is harmful to health in the long term. It is also unclear as to whether these materials can be recycled or whether they have to be deposited in landfills.

BRIEF SUMMARY OF THE INVENTION

It was therefore the object to provide a simple method for treating in particular the inner surfaces of a room, but also other condensation-promoting surfaces of building parts, possibly even only temporarily, in such a way that these treated surfaces of building parts have an inhibitory or even preventive effect on mold growth. The handling should be simple so that the formation of molds can be inhibited or suppressed rapidly—even if only temporarily. The aim of this method is not to eliminate the cause—for example cold bridges. The method is intended to be used in the transition phase up to the final elimination of the cause of the mold attack. It is for this reason that the handling is of decisive importance. Furthermore, the treated building parts should not release any toxic or slightly poisonous substances by evaporation, i.e. the use of preservatives or fungicides should be dispensed with in this method.

Surprisingly, it was found that the application of hydrophobic particles to the surface of building parts effectively suppresses mold formation. That the condensed atmospheric humidity rolls off the building part treated according to the invention, owing to the hydrophobicity of the applied particles, is advantageous here. Porous building parts continue to be breathable in spite of the applied hydrophobic particles, so that a certain proportion of the atmospheric humidity can be released via the building part to the outside air. By means of the method according to the invention, recurring moistening by dripping wetness, precipitated water or condensation on building parts can be avoided so that the molds lack the water which they require for their growth. The method according to the invention and the composition according to the invention which inhibits mold growth cannot be used if the moisture travels out of the building part itself to the surface thereof; this is the case with waterlogging or capillary condensation in the masonry. Furthermore, the method according to the invention is distinguished by its simple handling. A further advantage arises from the fact that the use of fungicides is dispensed with in the method according to the invention.

The present invention therefore relates to a method for suppressing mold formation on building parts using hydrophobic substances, wherein a dispersion of hydrophobic particles having a mean particle diameter of from 0.005 to 5 μm in an organic dispersant is applied to the surface to be protected from mold attack and the dispersant is then removed.

The present invention also relates to a composition for building parts which inhibits mold growth and which comprises from 0.1 to 10% by weight of hydrophobic particles having a mean particle diameter of from 0.005 to 5 μm dispersed in an organic dispersant.

DETAILED DESCRIPTION OF THE PREFERRED EMBODIMENTS

Figure 1:
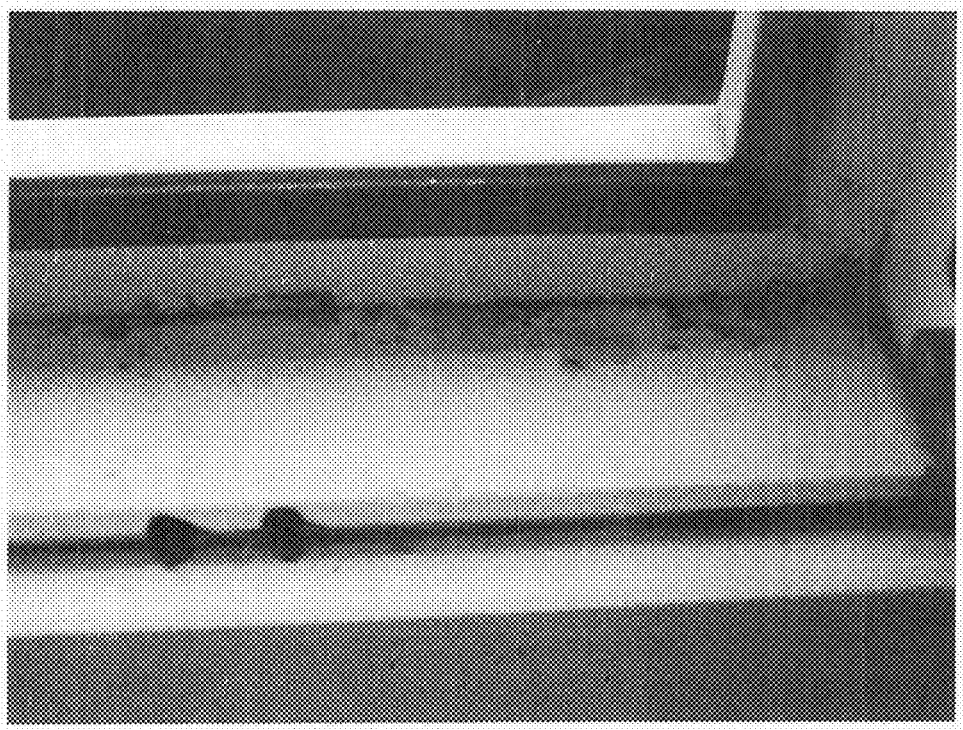
FIG. 1 shows the right half of a window which was not treated with a dispersion of the invention where molds are clearly recognizable.

The method according to the invention and the composition according to the invention which inhibits mold growth have the advantage that no long-lasting drying at a relatively high temperature is necessary, as is the case, for example, in WO 01/48098. A further advantage is that the modification or coating of the building parts by the method according to the invention can be applied subsequently. Thus, no problems with regard to the adhesion of wallpapers, paints or other applications to the modified plaster, which possibly now has hydrophobic properties, can occur.

The method according to the invention is based on the discovery of the lotus effect—the self-cleaning of surfaces.

The principle of self-cleaning and water-repellent surfaces is generally known. In order to achieve good self-cleaning of a surface, said surface must also have a certain roughness in addition to a very hydrophobic surface. A suitable combination of structure and hydrophobicity makes it possible for even small amounts of moving water to carry away dirt particles adhering to the surface and to clean the surface (WO 96/04123; U.S. Pat. No. 3,354,022).

According to EP 0 933 388, the prior art is that an aspect ratio of >1 and a surface energy of <20 mN/m are required for such self-cleaning and water-repellent surfaces. Here, the aspect ratio is defined as the quotient of height and width of the structure. The abovementioned criteria are realized in nature, for example on the lotus leaf. The plant surface which is formed from a hydrophobic waxy material has elevations which are a few μm apart. Water drops come into contact substantially only with the peaks of the elevations. Such repellent surfaces are widely described in the literature.

European Patent EP 0 990 015 B1 describes a transparent facade coating material which comprises at least one synthetic, nanoscale sheet silicate forming a colloidal gel with water. This coating material is said to reduce the tendency of a facade to become soiled. The particle size of the nanoscale sheet silicate is from 5 to 800 nm.

The method according to the invention for suppressing mold formation in buildings using hydrophobic substances is distinguished by the fact that a dispersion of hydrophobic particles having a mean particle diameter of from 0.005 to 5 μm, preferably from 0.005 to 1 μm, particularly preferably from 0.005 to 0.5 μm (the particles are defined according to DIN 53 206), in an organic dispersant is applied to the surface to be protected from mold attack and the dispersant is then removed.

The hydrophobic particles used in the method according to the invention preferably have a surface having an irregular fine structure in the nanometer range, i.e. in the range from 1 nm to 1000 nm, preferably from 2 nm to 750 nm and particularly preferably from 10 nm to 100 nm. Fine structure is understood as meaning structures which have elevations, teeth, fissures, burrs, cracks, undercuts, notches and/or holes with the abovementioned spacings and ranges. The fine structure of the hydrophobic particles can preferably have elevations with an aspect ratio greater than 1, particularly preferably greater than 1.5. The aspect ratio in turn is defined as the quotient of maximum height and maximum width of the elevation; in the case of burrs or other elongated elevations, the width transverse to the longitudinal direction is used. Hydrophobic particles which may be used in the method according to the invention are those which comprise at least one material selected from silicates, minerals, metal oxides, metal powders, silicic acids, pigments or polymers. Hydrophobic particles which can preferably be used are those which comprise a material selected from silica, alumina, titanium oxide, zirconium oxide, polytetrafluoroethylene homopolymer, polytetra-fluoroethylene copolymers or mixtures thereof, or silicates, doped silicates, minerals, silicic acids, Aerosils® or pulverulent polymers, such as, for example, spray-dried and agglomerated emulsions or cryomilled PTFE. Hydrophobic silicic acids, in particular hydrophobic pyrogenic silicic acids, are particularly preferably used as hydrophobic particles.

The hydrophobic properties of the particles may be present inherently owing to the particle material used, such as, for example, in the case of polytetrafluoro-ethylene (PTFE). However, it is also possible to use hydrophobic particles which have hydrophobic properties after a suitable treatment, such as, for example, particles treated with at least one compound from the group consisting of the fluoroalkylsilanes, of the alkylsilanes, of the perfluoroalkylsilanes, of the paraffins, of the waxes, of the fatty acid esters, of the functionalized long-chain alkane derivatives or of the alkyldisilazanes. Particularly suitable particles are hydrophobic pyrogenic silicic acids, so-called Aerosils®. Examples of hydrophobic particles are, for example, Aerosil® VPR 411, Aerosil® R202, Aerosil® VPLE 8241, aeroxides LE1 or Aerosil® R 8200. Examples of particles which can be rendered hydrophobic by treatment with perfluoroalkylsilane and subsequent heating are, for example, Aeroperl® 90/30, Sipernat® silicic acid 350, Aluminiumoxid® C, vanadium-doped zirconium silicate or Aeroperl® P 25/20.

All dispersants which are liquid at room temperature, in particular alcohols, preferably ethanol and/or isopropanol, can be used as organic dispersants for the dispersion used in the method according to the invention. Ethanol is particularly preferably used as the alcohol. However, it may also be advantageous if the dispersion comprises a mixture of different alcohols.

A dispersion of hydrophobic particles which preferably comprises from 0.1 to 10% by weight, preferably from 0.5 to 5% by weight and particularly preferably from 1.0 to 2.5% by weight of hydrophobic particles, based on the dispersant, is preferably used in the method according to the invention.

In addition to the dispersant and the hydrophobic particles, the dispersion used in the method according to the invention may comprise further components. In particular, they may comprise adhesion promoters. Preferably, however, the dispersions used comprise no adhesion promoters.

In the method according to the invention, the dispersion can be applied to surfaces of building parts, preferably to surfaces of walls or ceilings of a building consisting of stone, concrete, bricks, plaster, sandwich-type plasterboard, joints, paper-based wallpapers and/or mineral paints. This can be effected by spraying on, painting on or applying by means of a roller. In a particular embodiment of the method according to the invention, it is also possible to treat building parts of plastics or having a plastic surface, such as, for example, window frames.

In a preferred embodiment of the method according to the invention, the application of the dispersion is effected by spraying on. The spraying on of the dispersion is preferably effected by means of a spray apparatus which has a nozzle having a diameter of from 0.05 to 2 mm, preferably having a diameter of from 0.1 to 0.9 mm. The spraying of the suspension is preferably effected at a pressure of from 1 to 10 bar, particularly preferably at a pressure of from 1 to 5 bar. In particular, a propane/butane mixture may be used as propellant.

The removal of the organic dispersant is preferably effected by evaporation or volatilization at room temperature.

The present invention furthermore relates to a composition for building parts which inhibits mold growth, which composition comprises from 0.1 to 10% by weight of hydrophobic particles having a mean particle diameter of from 0.005 to 5 μm, preferably from 0.005 to 1 μm, particularly preferably from 0.005 to 0.5 μm (the particles are defined according to DIN 53 206), dispersed in an organic dispersant.

The hydrophobic particles of the mold-inhibiting composition according to the invention preferably have a surface with an irregular fine structure in the nanometer range, i.e. in the range from 1 nm to 1000 nm, preferably from 2 nm to 750 nm and particularly preferably from 10 nm to 100 nm. Fine structure is understood as meaning structures which have elevations, teeth, fissures, burrs, cracks, undercuts, notches and/or holes with the abovementioned spacings and ranges. The fine structure of the hydrophobic particles can preferably have elevations with an aspect ratio greater than 1, particularly preferably greater than 1.5. The aspect ratio in turn is defined as the quotient of maximum height and maximum width of the elevation; in the case of burrs or other elongated elevations, the width transverse to the longitudinal direction is used.

The mold-inhibiting composition according to the invention comprises hydrophobic particles which comprise at least one material selected from silicates, minerals, metal oxides, metal powders, silicic acids, pigments or polymers. The mold-inhibiting composition can preferably comprise hydrophobic particles which comprise a material selected from silica, alumina, titanium oxide, zirconium oxide, polytetrafluoro-ethylene homopolymer, polytetrafluoroethylene copolymers or mixtures thereof, or silicates, doped silicates, minerals, silicic acids, Aerosils® or pulverulent polymers, such as, for example, spray-dried and agglomerated emulsions or cryomilled PTFE. Particularly preferably, it comprises silicic acids, in particular pyrogenic silicic acids, as hydrophobic particles.

The hydrophobic properties of the particles may be present inherently owing to the particle material used, such as, for example, in the case of polytetrafluoroethylene (PTFE). However, it is also possible for the composition according to the invention to contain hydrophobic particles which have hydrophobic properties after a suitable treatment, such as, for example, with at least one compound from the group consisting of the fluoroalkylsilanes, of the alkylsilanes, of the perfluoroalkylsilanes, of the paraffins, of the waxes, of the fatty acid esters, of the functionalized long-chain alkane derivatives or of the alkyldisilazanes. Particularly suitable particles are hydrophobic pyrogenic silicic acids, so-called Aerosils®. Examples of hydrophobic particles are, for example, Aerosil® VPR 411, Aerosile R202, aeroxides LE1, Aerosil® VPLE 8241 or Aerosil® R 8200. Examples of particles which can be rendered hydrophobic by treatment with perfluoroalkylsilane and subsequent heating are, for example, Aeroperl® 90/30, Sipernat® silicic acid 350, Aluminiumoxid C, vanadium-doped zirconium silicate or Aeroperl® P 25/20.

The composition according to the invention preferably comprises an alcohol as the organic dispersant. In principle, the composition according to the invention may comprise all alcohols which are liquid at room temperature, in particular ethanol and/or isopropanol. Particularly preferably, the composition according to the invention comprises ethanol as the alcohol. However, it may also be advantageous if the composition according to the invention comprises a mixture of different alcohols. The dispersants used for the dispersing need not be dried beforehand. Preferably, the composition according to the invention comprises from 0.1 to 10% by weight, preferably from 0.5 to 5% by weight and particularly preferably from 1.0 to 2.5% by weight of hydrophobic particles, based on the dispersant.

In addition to the dispersant and the hydrophobic particles, the composition according to the invention may comprise further components. In particular, the composition according to the invention may comprise adhesion promoters. Preferably, however, the composition according to the invention comprises no adhesion promoters. If the application of the composition according to the invention is effected by spraying on, said composition preferably contains a propellant, particularly preferably a propellant mixture comprising propane and butane.

The method according to the invention is described by way of example with reference to the following examples, without there being any intention to limit the invention thereto.

EXAMPLE

Figure 2:
FIG. 2 shows the left half of a window that was treated with a dispersion of the invention showing that no molds have settled.

A PVC window frame of a north-facing window of a test room which was used as a bedroom was coated on the left half with a dispersion of Aerosile® VPLE 8241 in ethanol by means of a spray. Based on the ethanol dispersant and the propane/butane propellant mixture, the concentration of Aerosil® VPLE 8241 was 0.94% by weight. The amount of Aerosil® VPLE 8241 applied was from 0.4 to 5 g/m² in tests in which test surfaces were analogously sprayed. For comparison, the right half remained untreated. Before the test, the window, including the window frame, was cleaned with a household cleaner of the Sidoline® type. The test took place in the period from Nov. 15, 2002 to Jan. 31, 2003 in Frankfurt/Main. The test room was an unheated room which, however, was protected from excessive cooling by a frost monitor. The picture in FIG. 1 shows the right half of the window, which was not treated according to the invention, after 3½ months, while the picture in FIG. 2 shows the left half of the window, which was treated according to the invention, after an identical time span. In the picture in FIG. 2, it is clearly evident that no molds have settled, in contrast to the picture in FIG. 1, in which the molds are clearly recognizable.

The invention claimed is:

1. A method for suppressing mold formation on a surface of a building part comprising:
  applying to the surface of a building part to be protected from mold, a dispersion comprising:
    a dispersant and
    hydrophobic particles having
      a mean particle diameter ranging from 0.005 to 5 μm,
      an irregular fine structure ranging from 1 nm to 1,000 nm,
      wherein elevations on the particles have an aspect ratio greater than 1; and
  removing the dispersant;
  wherein said dispersion is applied to a stone, bricks, concrete or plaster surface; or
  wherein said dispersion is applied to the surface of a sandwich plaster board, joints, paper-based wall papers, or mineral paint.

2. The method of claim 1, wherein elevations on the particles have an aspect ratio greater than 1.5.

3. The method of claim 1, wherein said dispersion is applied to a stone, concrete or plaster surface.

4. The method of claim 1, wherein said dispersion is applied to the surface of a sandwich plaster board, joints, paper-based wall papers, or mineral paint.

5. The method of claim 1, wherein said dispersion is applied by spraying it on the surface.

6. The method of claim 1, wherein said dispersant is removed by evaporation or volatilization.

7. The method of claim 1, wherein said dispersion comprises from 0.1 to 10% by weight, based on the weight of the dispersant, of the hydrophobic particles.

8. The method of claim 1, wherein said dispersion comprises at least one type of hydrophobic particles selected from the group consisting of silica, alumina, titanium oxide, and zirconium oxide; or mixtures thereof.

9. The method of claim 1, wherein said dispersion comprises hydrophobic particles that are silicic acid or pyrogenic silicic acid.

10. The method of claim 1, wherein said dispersion comprises hydrophobic particles that are silicic acid or pyrogenic silicic acid that have been treated with at least one agent selected from the group consisting of fluoroalkylsilanes, alkylsilanes, perfluoroalkylsilanes, and alkyldisilazanes.

11. The method of claim 1, wherein said dispersion comprises at least one type of hydrophobic particles selected from the group consisting of polytetrafluoroethylene homopolymer and polytetrafluoroethylene copolymers; or mixtures thereof.

12. The method of claim 1, wherein the dispersant comprises ethanol, isopropanol, or a combination thereof.

13. The method of claim 1, wherein said hydrophobic particles have a mean particle diameter ranging from 0.005 to 0.5 μm.

14. The method of claim 1, wherein said hydrophobic particles have an irregular fine structure ranging from 10 nm to 100 nm.

15. A self-cleaning lotus-effect surface of a building part produced by applying a composition comprising an organic dispersant, and hydrophobic particles in an amount ranging from 0.1 to 10% by weight of the composition having
a mean particle diameter of from 0.005 to 5 μm,
an irregular fine structure ranging from 1 nm to 1,000 nm, wherein elevations on the particles have an aspect ratio greater than 1
to a surface of a building part and removing the organic dispersant, thus producing a self-cleaning lotus-effect surface;
wherein said surface of a building part comprises a stone, concrete, brick, plaster, sandwich plaster board, joint, paper-based wall paper, or mineral paint.

16. The self-cleaning lotus-effect surface of claim 15, wherein said composition does not contain hydrophobic titanium oxide particles.

17. A stone, concrete, brick, plaster, sandwich plaster board, joint, paper-based wall paper, or mineral paint surface of a building part comprising a composition comprising:
hydrophobic particles having a mean particle diameter of from 0.005 to 5 μm, an irregular fine structure ranging from 1 nm to 1,000 nm, wherein elevations on the particles have an aspect ratio greater than 1 in an amount ranging from 0.1 to 10% by weight of the composition.

* * * * *